(12) United States Patent
Rao et al.

(10) Patent No.: US 9,689,996 B2
(45) Date of Patent: Jun. 27, 2017

(54) INTEGRATED DIODE DAS DETECTOR

(71) Applicant: General Electric Company, Schnectady, NY (US)

(72) Inventors: Naresh Kesavan Rao, Niskayuna, NY (US); James Wilson Rose, Niskayuna, NY (US); Christopher David Unger, Milwaukee, WI (US); Abdelaziz Ikhlef, Waukesha, WI (US); Jonathan David Short, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 606 days.

(21) Appl. No.: 13/857,624

(22) Filed: Apr. 5, 2013

(65) Prior Publication Data
US 2014/0301534 A1 Oct. 9, 2014

(51) Int. Cl.
*A61B 6/00* (2006.01)
*G01T 1/24* (2006.01)
*H01L 27/146* (2006.01)

(52) U.S. Cl.
CPC .......... *G01T 1/247* (2013.01); *A61B 6/42* (2013.01); *H01L 27/14661* (2013.01); *H01L 27/14663* (2013.01); *A61B 6/4233* (2013.01)

(58) Field of Classification Search
CPC ..... G01T 1/2006; G01T 1/247; G01T 1/2928; H01L 27/14658; A61B 6/42; A61B 6/4233
See application file for complete search history.

(56) References Cited

U.S. PATENT DOCUMENTS 6,215,843 B1   4/2001  Saito et al.
6,366,231 B1   4/2002  Rao et al.
(Continued)

FOREIGN PATENT DOCUMENTS

CN   101788680 A  *  7/2010
EP     2560026 A1    2/2013
WO  2004027454 A1    4/2004

OTHER PUBLICATIONS

Search Report and Written Opinion from Corresponding PCT Application No. PCT/US2014/032962 dated Jul. 10, 2014.
(Continued)

*Primary Examiner* — Glen Kao
(74) *Attorney, Agent, or Firm* — Pabitra K. Chakrabarti (57) ABSTRACT

Improved imaging systems are disclosed. More particularly, the present disclosure provides for an improved image sensor assembly for an imaging system, the image sensor assembly having an integrated photodetector array and its associated data acquisition electronics fabricated on the same substrate. By integrating the electronics on the same substrate as the photodetector array, this thereby reduces fabrications costs, and reduces interconnect complexity. Since both the photodiode contacts and the associated electronics are on the same substrate/plane, this thereby substantially eliminates certain expensive/time-consuming processing techniques. Moreover, the co-location of the electronics next to or proximal to the photodetector array provides for a much finer resolution detector assembly since the interconnect bottleneck between the electronics and the photodetector array is substantially eliminated/reduced. The co-location of the electronics next to or proximal to the photodetector array also enables/facilitates programmable pixel configuration for optimal image quality.

20 Claims, 5 Drawing Sheets

(56) References Cited

U.S. PATENT DOCUMENTS

| | | |
|---|---|---|
| 6,510,195 B1* | 1/2003 | Chappo et al. .................. 378/19 |
| 6,522,395 B1 | 2/2003 | Bamji et al. |
| 6,608,311 B1 | 8/2003 | Roziere et al. |
| 6,958,474 B2 | 10/2005 | Laprade et al. |
| 7,095,354 B2 | 8/2006 | Harrison et al. |
| 7,362,849 B2 | 4/2008 | Short et al. |
| 7,403,590 B2 | 7/2008 | Possin et al. |
| 7,935,933 B2 | 5/2011 | Hoffman |
| 7,936,299 B2 | 5/2011 | Astley et al. |
| 8,039,811 B1 | 10/2011 | Li et al. |
| 2004/0016885 A1* | 1/2004 | Ikhlef ........................... 250/367 |
| 2004/0036775 A1* | 2/2004 | Watson et al. .............. 348/207.1 |
| 2005/0236573 A1* | 10/2005 | Vogtmeier ................ 250/370.09 |
| 2005/0285043 A1* | 12/2005 | Nascetti et al. .......... 250/370.09 |
| 2007/0176108 A1 | 8/2007 | Such et al. |
| 2011/0158387 A1 | 6/2011 | Narayanaswamy et al. |
| 2012/0069954 A1* | 3/2012 | Iso ........................... A61B 6/03 378/7 |

OTHER PUBLICATIONS

Turchetta et al., "A Monolithic Active Pixel Sensor for Charged Particle Tracking and Imaging Using Standard VLSI CMOS Technology", Nuclear Instruments and Methods in Physics Research, pp. 677-689, vol. 458, Issue 3, Feb. 11, 2001.

Steadman et al., "A CMOS Photodiode Array with in-pixel Data Acquisition System", Solid-State Circuits Conference, 2003. ESSCIRC '03. Proceedings of the 29th European, pp. 117-120, Sep. 2003.

Steadman et al., "An In-Pixel Current-Mode Amplifier for Computed Tomography", Sensors Journal, IEEE, pp. 1372-1373, vol. 6, Issue 6, Dec. 2006.

* cited by examiner

INTEGRATED DIODE DAS DETECTOR

BACKGROUND

1. Technical Field

The present disclosure relates to imaging systems and, more particularly, to an image sensor assembly for an imaging system, the image sensor assembly having an integrated photodetector array and its associated data acquisition electronics fabricated on the same substrate.

2. Background Art

In general, computed tomography ("CT") may be utilized for a wide variety of imaging applications, such as, for example, medical imaging applications. CT imaging systems are typically configured to transmit radiation (e.g., x-rays) through a structure (e.g., a human body) to detect and/or diagnose abnormalities (e.g., tumors). In general, these low energy x-rays are subsequently received and processed to formulate an image, often three-dimensional, of the body structure that may be analyzed by users as a diagnostic aid or the like.

In general, the reception of the radiation (e.g., gamma rays or x-rays) is sometimes accomplished through the use of a device such as a detector assembly or the like. The detector assembly typically includes a plurality of structures working together to receive and process the incoming energy rays after they have passed through the body structure. For example, the detector assembly typically utilizes a scintillator assembly to convert incident radiation (e.g., x-rays) into light for detection at an array of light detection devices. In general, scintillation allows the radiation received by the scintillator assembly to be converted into useful information. The light produced by the scintillator assembly is typically received/detected and processed by a detection device/assembly (e.g., a light sensitive photodiode array), which converts the light from the scintillator assembly into an electronic signal. As such, the information from the scintillator assembly can be transferred, converted, and processed by electronic modules in a data acquisition system ("DAS") to facilitate viewing and manipulation by users.

For example, in some CT imaging systems, an x-ray source emits a beam toward a subject or object (e.g., a patient). The beam, after being attenuated by the subject/object, impinges upon an array of radiation detectors. The intensity of the attenuated beam radiation received at the detector array is typically dependent upon the attenuation of the x-ray beam by the subject. Each detector element of the detector array typically produces a separate electrical signal indicative of the attenuated beam received by each detector element. The electrical signals are transmitted to a data processing system for analysis which ultimately produces an image.

As noted, each detector element may be characterized by a scintillator cell that releases light in response to the reception of x-rays. In general, the light is collected by a photodiode, which provides an electrical signal output that is indicative of the x-rays impinged by the scintillator cell. Charge generated from the sensed light is then transmitted to a DAS, either directly, or through a FET switch array. Some CT detectors include thousands of detector elements and, as a result, a comparable number of connections to a comparable number of detector elements share a common DAS input channel. Other known detectors provide charge storage at each pixel and share a single amplifier among many pixels.

In general, the number of pixels in a CT detector is increasing exponentially, which directly impacts the interconnect between the photodiode array and the sensitive electronics. In current CT imaging systems, the array of light detection devices (e.g., photodiodes) are attached to the electronics/electronic modules in a DAS by utilizing packaging, or wafer to wafer bonding. Stated another way, the photodiode array is fabricated on a first wafer and then attached to a second wafer having an array of electronics by wafer to wafer bonding, or the photodiode array is attached to a package with an area interconnect.

Thus, an interest exists for improved imaging systems and methods. These and other inefficiencies and opportunities for improvement are addressed and/or overcome by the systems, assemblies and methods of the present disclosure.

SUMMARY

The present disclosure provides advantageous imaging systems. In exemplary embodiments, the present disclosure provides for an improved image sensor assembly for an imaging system, the image sensor assembly having an integrated photodetector array and its associated data acquisition electronics fabricated on the same substrate (e.g., on a single wafer die).

By integrating the electronics (e.g., DAS electronics) on the same substrate (e.g., silicon wafer die) as the photodetector array (e.g., photodiode array), fabrication costs and interconnect complexity can be reduced. More particularly, since both the photodiode contacts and the associated electronics are on the same substrate/plane, expensive and/or time-consuming processing techniques such as, for example, Through-Silicon Vias ("TSVs") processing techniques can be avoided/eliminated. Moreover, the co-location of the electronics next to or proximal to the photodetector array provides for a much finer resolution detector assembly since the interconnect bottleneck between the electronics and the photodetector array is substantially eliminated/reduced. The co-location of the electronics next to or proximal to the photodetector array also enables/facilitates programmable pixel configuration for optimal image quality.

The present disclosure provides for an image sensor assembly including a substrate; a plurality of photodetectors disposed on the substrate, the plurality of photodetectors in electrical communication with data acquisition and signal processing electronic components on the substrate; a structured scintillator assembly disposed over the plurality of photodetectors; and a collimator assembly positioned with respect to the plurality of photodetectors and the data acquisition and signal processing electronic components; wherein a layout of the photodetectors and the data acquisition and signal processing electronic components and a structural configuration of the collimator assembly are defined with respect to each other.

The present disclosure also provides for an image sensor assembly wherein at least a portion of the collimator assembly is positioned over at least a portion of the data acquisition and signal processing electronic components on the substrate to shield at least a portion of the data acquisition and signal processing electronic components from radiation.

The present disclosure also provides for an image sensor assembly wherein the substrate (e.g., the passivation layer) includes a plurality of dimpled areas, the scintillator conforming to the dimpled areas, the dimpled areas narrowing in area from a top side to a bottom side of the scintillator assembly.

The present disclosure also provides for an image sensor assembly that is incorporated into a detector assembly of an imaging system. The present disclosure also provides for an image sensor assembly wherein the data acquisition and signal processing electronic components further includes front end circuitry for each photodetector; and back end circuitry in electrical communication with the front end circuitry; wherein the back end circuitry is configured to multiplex the output signals of the front end circuitry for each photodetector.

The present disclosure also provides for an image sensor assembly wherein the back end circuitry is configured to process the output signals in sequence. The present disclosure also provides for an image sensor assembly wherein the output of the back end circuitry combines the outputs of the front end circuitry for each photodetector into a single channel.

The present disclosure also provides for an image sensor assembly wherein each photodetector is in electrical communication with an energy storage device, each energy storage device in electrical communication with front end circuitry; and wherein the front end circuitry processes the charge from each energy storage device in sequence. The present disclosure also provides for an image sensor assembly wherein a quantity of the photodetectors are adapted to be selectively combined to form one or more pixels.

The present disclosure also provides for a method of fabricating an image sensor assembly including providing a substrate; disposing a plurality of photodetectors on the substrate; integrating data acquisition and signal processing electronic components on the substrate, the data acquisition and signal processing electronic components in electrical communication with the plurality of photodetectors; positioning a structured scintillator assembly over the plurality of photodetectors; and positioning a collimator assembly with respect to the plurality of photodetectors and the data acquisition and signal processing electronic components; wherein a layout of the photodetectors and the data acquisition and signal processing electronic components and a structural configuration of the collimator assembly are defined with respect to each other.

The present disclosure also provides for a method of fabricating an image sensor assembly wherein at least a portion of the collimator assembly is positioned over at least a portion of the data acquisition and signal processing electronic components on the substrate to shield at least a portion of the data acquisition and signal processing electronic components from radiation.

The present disclosure also provides for a method of fabricating an image sensor assembly wherein the substrate (e.g., the passivation layer) includes a plurality of dimpled areas, the scintillator conforming to the dimpled areas, the dimpled areas narrowing in area from the top side to the bottom side of the scintillator assembly. The present disclosure also provides for a method of fabricating an image sensor assembly further including the step of incorporating the fabricated image sensor assembly into a detector assembly of an imaging system.

The present disclosure also provides for a method of fabricating an image sensor assembly wherein the data acquisition and signal processing electronic components include front end circuitry for each photodetector and back end circuitry in electrical communication with the front end circuitry, and the method further includes configuring the back end circuitry to multiplex the output signals of the front end circuitry for each photodetector.

The present disclosure also provides for a method of fabricating an image sensor assembly further including disposing a plurality of energy storage devices on the substrate, each photodetector being in electrical communication with one of the energy storage devices, each energy storage device in electrical communication with front end circuitry; and configuring the front end circuitry to process the charge from each energy storage device in sequence.

The present disclosure also provides for a method of fabricating an image sensor assembly further including selectively combining a quantity of the photodetectors to form one or more pixels.

The present disclosure also provides for an imaging system including an x-ray source; and an image sensor assembly including: (a) a substrate; (b) a plurality of photodetectors on the substrate, the plurality of photodetectors in electrical communication with data acquisition and signal processing electronic components on the substrate; (c) a structured scintillator assembly disposed over the plurality of photodetectors; and (d) a collimator assembly positioned with respect to the plurality of photodetectors and the data acquisition and signal processing electronic components; wherein the scintillator assembly is configured to: (i) receive x-rays that pass through an object, the x-rays emitted from the x-ray source, and (ii) release light at an intensity in response to reception of x-rays; wherein each photodetector of the plurality of photodetectors is configured to provide an electrical signal indicative of the intensity of the light released by the scintillator assembly and received by each photodetector; and wherein a layout of the photodetectors and the data acquisition and signal processing electronic components and a structural configuration of the collimator assembly are defined with respect to each other.

The present disclosure also provides for an imaging system wherein at least a portion of the collimator assembly is positioned over at least a portion of the data acquisition and signal processing electronic components on the substrate to shield at least a portion of the data acquisition and signal processing electronic components from radiation.

The present disclosure also provides for an imaging system wherein the substrate (e.g., the passivation layer) includes a plurality of dimpled areas, the scintillator assembly conforms to the dimpled areas, the dimpled areas narrowing in area from a top side to a bottom side of the scintillator assembly. The present disclosure also provides for an imaging system wherein the data acquisition and signal processing electronic components further include front end circuitry for each photodetector; and back end circuitry in electrical communication with the front end circuitry; wherein the back end circuitry is configured to multiplex the output signals of the front end circuitry for each photodetector, process the output signals in sequence, and combine the outputs of the front end circuitry for each photodetector into a single channel.

Any combination or permutation of embodiments is envisioned. Additional advantageous features, functions and applications of the disclosed systems, assemblies and methods of the present disclosure will be apparent from the description which follows, particularly when read in conjunction with the appended figures. All references listed in this disclosure are hereby incorporated by reference in their entireties.

BRIEF DESCRIPTION OF THE DRAWINGS

Exemplary embodiments of the present disclosure are further described with reference to the appended figures. It is to be noted that the various steps, features and combinations of steps/features described below and illustrated in the figures can be arranged and organized differently to result in embodiments which are still within the spirit and scope of the present disclosure. To assist those of ordinary skill in the art in making and using the disclosed systems, assemblies and methods, reference is made to the appended figures, wherein.

DETAILED DESCRIPTION

In the description which follows, like parts are marked throughout the specification and drawings with the same reference numerals, respectively. Drawing figures are not necessarily to scale and in certain views, parts may have been exaggerated for purposes of clarity.

The present disclosure provides improved imaging systems (e.g., radiographic imaging systems). More particularly, the present disclosure provides for an advantageous image sensor assembly for an imaging system, the image sensor assembly having an integrated photodetector array and its associated data acquisition electronics fabricated on the same substrate (e.g., the same die). In exemplary embodiments of the present disclosure, the advantageous image sensor assembly is incorporated into a detector assembly of an imaging system.

Current practice provides that the number of pixels in a CT detector is increasing exponentially, which directly impacts the interconnect between the photodiode array and the sensitive electronics. Current practice also provides that the array of light detection devices in CT imaging systems are separately fabricated from and attached to the electronics/electronic modules in a DAS by utilizing packaging, or wafer to wafer bonding.

In general, the present disclosure provides for improved image sensor assemblies for an imaging system, the image sensor assemblies having an integrated photodetector array and its associated data acquisition electronics fabricated on the same substrate, thereby providing a significant commercial, operational and/or manufacturing advantage as a result.

More particularly, by integrating the electronics on the same substrate as the photodetector array, fabrication costs and interconnect complexity can be reduced. For example, since both the photodiode contacts and the associated electronics are on the same substrate/plane, certain expensive/time-consuming processing techniques (e.g., TSVs processing) can be substantially eliminated. Moreover, the co-location of the electronics next to or proximal to the photodetector array provides for a much finer resolution detector assembly since the interconnect bottleneck between the electronics and the photodetector array is substantially eliminated/reduced. The co-location of the electronics next to or proximal to the photodetector array also enables/facilitates programmable pixel configuration for optimal image quality.

Since the electronics are placed next to the photodiode array, this may reduce the photodiode area in certain embodiments. However, by utilizing a scintillator assembly (e.g., structured scintillator assembly) as discussed further below, the light is advantageously guided into the photodiodes for better/improved efficiency. Stated another way and as discussed further below, the advantageous structured scintillator assembly, which guides the light into the photodetector array, is utilized to offset any loss of photodetector area (e.g., loss of area due to the accommodation of the electronics on the wafer/substrate).

As noted above, the number of pixels in a CT detector is increasing exponentially, which directly impacts the interconnect between the photodiode array and the sensitive electronics, and current practice provides that the photodiode array is attached to the electronics by utilizing packaging or wafer to wafer bonding. In exemplary embodiments, the present disclosure advantageously eliminates/reduces the interconnect by fabricating the electronics and the photodetector array on the same substrate (e.g., the electronics are fabricated in the gaps between photodiodes of the substrate). Such an approach also reduces costs, since the photodetectors and the electronics are fabricated at substantially the same time. It also reduces interconnect capacitance between the photodetector array and the electronics, thereby greatly improving performance in terms of noise, speed and power dissipation. Such an approach is also one of the keys in improving the problems associated with the trend of having an increasing number of pixels in a CT detector/system.

As discussed further below, the systems, assemblies and methods of the present disclosure substantially overcome the interconnect bottleneck between photodetectors and their associated electronics. The systems, assemblies and methods of the present disclosure also reduce power dissipation, reduce noise and increase speed due to, inter alia, the reduced interconnect capacitance. The systems, assemblies and methods of the present disclosure also allow for the multiplexing of several pixels into a single channel of electronics to reduce power and/or a number of electronic components required to process signals from the photodetectors. The systems, assemblies and methods of the present disclosure also reduce costs by substantially eliminating the interconnect, and reduce/eliminate expensive thermal management. Moreover, the systems, assemblies and methods of the present disclosure enable an integrated digital sensor which improves robustness to interference.

Figure 1:
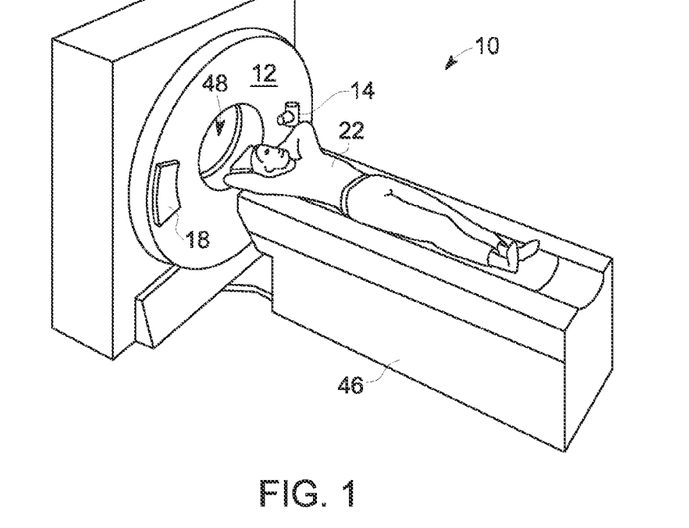
FIG. 1 is an illustration of a computed tomography imaging system which may include an image sensor assembly in accordance with exemplary embodiments of the present disclosure.
Figure 2:
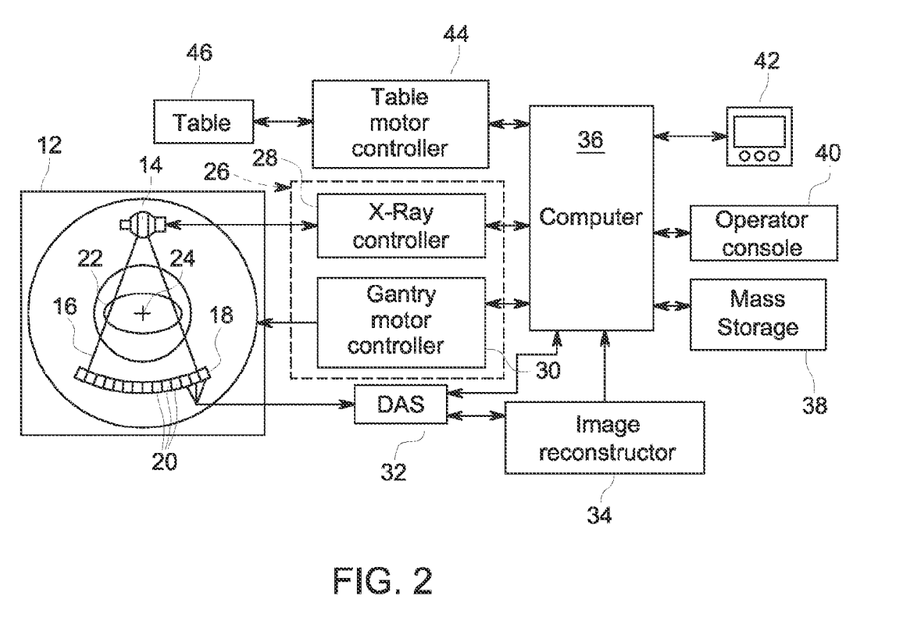
FIG. 2 is a block diagram of the imaging system of FIG. 1.

Referring now to the drawings, and in particular to FIGS. 1-2, an exemplary computed tomography (CT) imaging system 10 which may employ a detector array 18 is shown. It is to be noted that although a certain CT imaging system 10 has been illustrated, it should be understood that the image sensor assemblies 20 and/or detector array 18 of the present disclosure may be utilized in a wide variety of imaging systems.

In exemplary embodiments, the CT imaging system 10 includes a scanner assembly 12 illustrated as a gantry assembly. Gantry 12 has an x-ray source 14 that projects a fan beam of x-rays 16 toward a detector array 18 on the opposite side of the gantry 12. Detector array 18 is formed by a plurality of detector modules or image sensor assemblies 20 which together sense the projected x-rays that pass through a medical patient 22.

In certain embodiments and as discussed further below, each detector module/assembly 20 comprises an array of photosensitive elements or photodetectors 21 (FIG. 4), such as photodiodes or the like. Each photodetector 21 produces an electrical signal that represents the intensity of an impinging x-ray beam and hence the attenuated beam as it passes through the patient 22. In exemplary embodiments, during a scan to acquire x-ray projection data, gantry 12 and its associated components rotate about a center of rotation 24.

In general, rotation of gantry 12 and the operation of x-ray source 14 are governed by a control mechanism 26 of CT system 10. In exemplary embodiments, control mechanism 26 includes an x-ray controller 28 that provides power and timing signals to an x-ray source 14 and a gantry motor controller 30 that controls the rotational speed and position of gantry 12.

As discussed further below, data acquisition system (DAS) and signal processing electronic components 32 (FIG. 4) associated with or fabricated on each detector module/assembly 20 samples data (e.g., analog data) from the photodetectors 21 and converts the data to digital signals for subsequent processing. An image reconstructor 34 receives sampled and digitized x-ray data from the DAS electronic components 32 of each detector module/assembly 20, and performs high speed reconstruction. The reconstructed image may be applied as an input to a computer 36, which stores the image in a mass storage device 38.

Computer 36 also may receive commands and scanning parameters from an operator via console 40 that has a keyboard. An associated display 42 allows the operator to observe the reconstructed image and other data from computer 36. The operator supplied commands and parameters may be used by computer 36 to provide control signals and information to DAS electronic components 32, x-ray controller 28 and/or gantry motor controller 30. In addition, computer 36 may operate a table motor controller 44 which controls a motorized table 46 to position patient 22 and/or gantry 12. In general, table 46 moves portions of patient 22 through a gantry opening 48.

Figure 3:
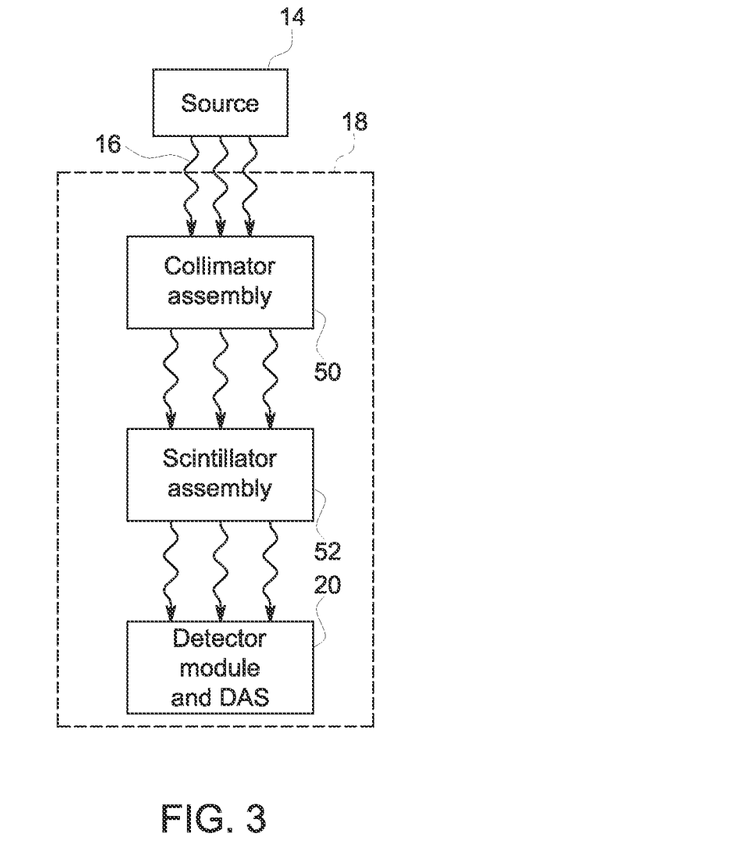
FIG. 3 is a partial block diagram of the imaging system of FIG. 1.

Referring now to FIG. 3, a partial block diagram of a detector array 18 which may be configured in accordance with exemplary embodiments of the present disclosure is shown. Detector array 18 includes at least one image sensor assembly or detector module 20, and typically includes a plurality of assemblies/modules 20 (FIG. 2).

As noted, each module 20 of detector assembly 18 typically receives x-rays 16 from a source 14 and transmits data to the DAS electronic components 32 located on each module 20. In general, each module 20 includes and/or is associated with a collimator assembly 50 and a scintillator assembly 52. During operation, x-rays 16 pass through an object such as a patient 22, then through the openings in the collimator assembly 50, and are subsequently received by the detector module 20. In exemplary embodiments, the collimator assembly 50 is generally configured to limit and define the direction and angular divergence of the x-rays 16 onto the scintillator assembly 52. In one embodiment, the collimator assembly 50 is fabricated from radiation absorbent material such as lead or tungsten or the like, although the present disclosure is not limited thereto. Rather, collimator assembly 50 may take a variety of forms.

Collimator assembly 50 is generally designed to reduce x-ray scatter and/or to shield the underlying elements from undesirable exposure. Stated another way, collimator assembly 50 is typically used to reduce x-ray scatter as the x-rays approach the scintillator assembly 52.

The x-rays 16 are directed through the collimator assembly 50 to the scintillator assembly 52. The scintillator assembly 52 is configured to convert the incident x-rays into light for detection by the underlying detector module 20.

Each detector module/assembly 20 typically includes a plurality of photodetectors 21, such as photodiodes or the like. The photodiodes 21 of each detector module 20 sense the incident light rays from the scintillator assembly 52 and convert the light rays into signals (e.g., analog signals), which are then transmitted to the DAS electronic components 32 located on each module 20. The electronic components 32 then convert the data (e.g., analog data) to signals (e.g., digital signals) for subsequent processing, as noted above.

Figure 4:
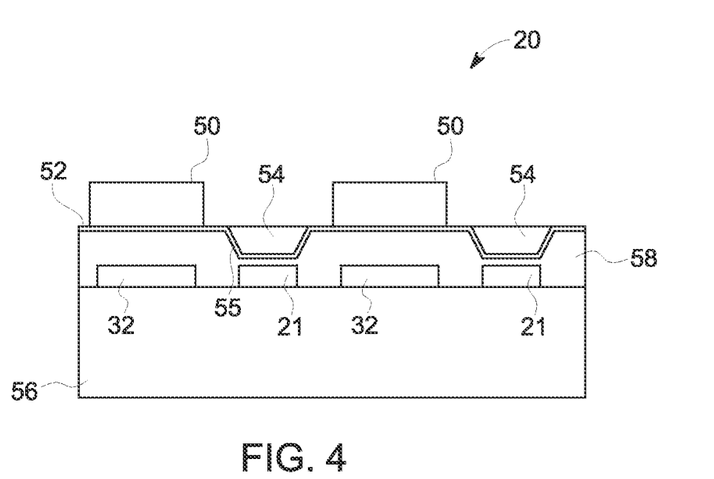
FIG. 4 is a side view of an image sensor assembly/detector module fabricated in accordance with exemplary embodiments of the present disclosure.
Figure 5:
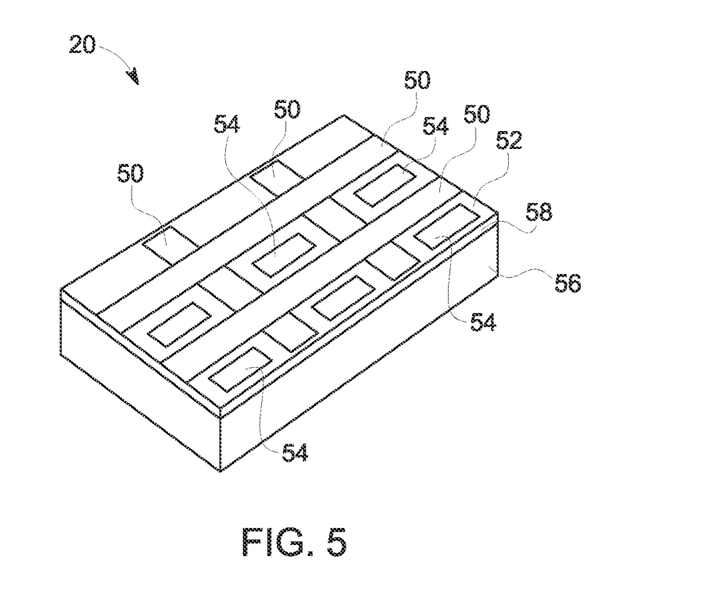
FIG. 5 is a top perspective view of the module of FIG. 4.

FIGS. 4-5 illustrate an image sensor assembly/detector module 20 fabricated in accordance with exemplary embodiments of the present disclosure. As previously described with respect to FIG. 3, each module 20 includes and/or is associated with a collimator assembly 50 and a scintillator assembly 52. In exemplary embodiments, the scintillator assembly 52 of each module 20 can include a plurality of scintillators 54 that are configured to illuminate upon the reception of x-rays.

In exemplary embodiments, the components of image sensor assembly/detector module 20 are typically fabricated within and/or on substrate 56 (e.g., semiconductor substrate). For example, in one embodiment a complementary metal oxide semiconductor (CMOS) process is utilized to generate a plurality or array of photodetectors 21 on substrate 56, although the present disclosure is not limited thereto. Substrate 56 may be, for example, a silicon wafer/die or the like.

A plurality of DAS and signal processing electronic components 32 may be integrated on substrate 56 with the photodetectors 21. For example, the gaps/areas between the photodiodes 21 may be used to integrate the electronics components 32 on substrate 56. In exemplary embodiments, each integrated electronic component 32 is configured and adapted to be in electrical communication with at least one photodetector 21 of the plurality of photodetectors 21 on substrate 56. In general, the array of photodetectors 21 and the integrated electronic components 32 constitute at least a portion of image sensor assembly/detector module 20. As noted, a plurality of modules 20 may be configured to define at least a portion of detector array 18 of system 10 (e.g., a plurality of modules 20 may be plugged into a motherboard or the like to define at least a section of detector array 18). As discussed further below, the output of the photodetectors 21 can be multiplexed to reduce the number of interconnects and/or electronic components 32 in a detector module 20, and therefore reduce the number of interconnects and/or electronic components 32 in the detector array 18 as well as to reduce a number of interconnects to other electronics on a motherboard from the detector array 18 fabricated separately from the detector array 18. In general, the multiplexed signals are either analog or digital signals. Moreover, the determination of the nature of the signals is determined by optimizing photodiode 21 area with the area of electronics 32 and thermal requirements. The on-chip signal processing electronics 32 may be multiplexed to process signals from multiple pixels, thereby reducing power and increasing diode 21 area. In exemplary embodiments, a single pixel may be sub-divided into multiple sub-pixels, and these sub-pixels can be selectively combined using switches or the like to realize optimal pixel geometries. In certain embodiments, a quantity of photodetectors 21 are configured and adapted to be selectively combined to form one or more pixels.

A scintillator assembly 52 is positioned and/or deposited over the plurality of photodetectors 21. In exemplary embodiments, the substrate 56 includes a passivation layer 58 or the like positioned and/or deposited over at least a portion of the bulk substrate (e.g., silicon wafer or die) and/or photodetectors 21 (e.g., over at least a portion of the top side of substrate 56). In certain embodiments, the substrate 56 (e.g., passivation layer 58 of substrate 56) includes a plurality of dimpled areas 55 with the structured scintillator assembly 52 conforming to the dimpled areas 55. The dimpled areas 55 narrow in area from a top side to a bottom side of the scintillator assembly 52. As such, each scintillator 54 of structured scintillator assembly 52 is configured so that the top side of the scintillator 54 is wider than the bottom side of the scintillator 54 (e.g., in the shape of an inverse trapezoid or the like). In general, the scintillators 54 of structured scintillator assembly 52 are configured to guide light into the photodetectors 21, and this configuration may be advantageously utilized to offset any loss of photodiode area to accommodate for the DAS electronics 32 on substrate 56.

As shown in FIGS. 4-5, a collimator assembly 50 is then positioned with respect to the plurality of photodetectors 21 and the DAS and signal processing electronic components 32. For example, the collimator assembly 50 is typically positioned over the top side of the substrate 56 and the scintillator assembly 52. In exemplary embodiments, a layout of the photodetectors 21 and the electronic components 32 on the substrate 56 and a structural configuration of the collimator assembly 50 are defined with respect to each other. As one example, the layout of the photodetectors 21 and the electronic components 32 can be determined based on the structural configuration of the collimator assembly 50 so that when the collimator 50 is disposed over the top side of the substrate 56, the collimator substantially covers the electronic components 32, but not the photodetectors 21. As another example, the structural configuration of the collimator 50 can be determined based on the layout of the photodetectors 21 and the electronic components 32 so that when the collimator 50 is disposed over the top side of the substrate 56, the collimator substantially covers the electronic components 32, but not the photodetectors 21. In certain embodiments of the present disclosure, at least a portion of the collimator assembly 50 is positioned over at least a portion of the electronic components 32 to shield at least a portion of the electronic components 32 from radiation (e.g., x-rays) 16. Stated another way, by placing the electronic components 32 under the collimator assembly (e.g., collimation grid) 50, this advantageously provides that the electronic components are more robust and/or protected to radiation damage (e.g., from source 14).

In exemplary embodiments, one or more dummy diodes can be disposed with respect to the substrate 56, which can be covered by the collimator 50 and configured to provide a signal corresponding to the temperature of the substrate 56 and/or module 20 to provide for thermal management. For example, the one or more dummy diodes can be arranged in a forward bias mode of operation. If the temperature of the substrate and/or module increase the current flowing through the diode can increase according to a thermal coefficient. The current can be measured to determine the temperature of the surroundings of the dummy diodes.

Figure 6:
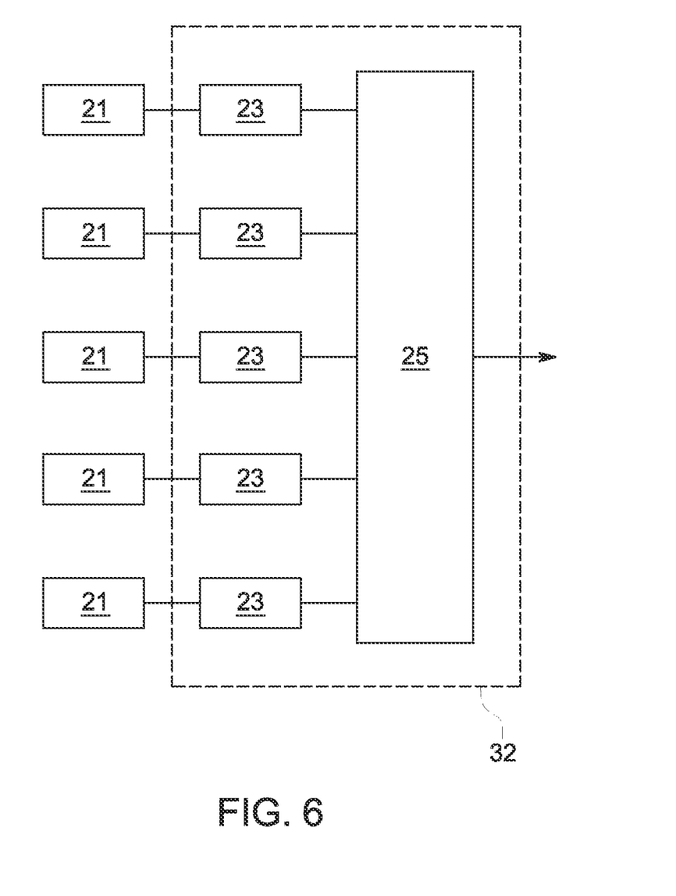
FIG. 6 is a partial block diagram of photodetectors and electronic components of an image sensor assembly/detector module in accordance with an exemplary embodiment of the present disclosure.

In exemplary embodiments and as shown in FIG. 6, the DAS and signal processing electronic components 32 of module 20 may include front end circuitry 23 for each photodetector 21, and back end circuitry 25 in electrical communication with and common to the front end circuitry 23 for each photodetector 21. The front end circuitry 23 can include, for example, buffers, amplifiers, filters, and the like, and the back end circuitry 25 can include analog-to-digital converters, amplifiers, timing control circuitry, and the like. In certain embodiments, back end circuitry 25 is configured and adapted to multiplex the output signals of the front end circuitry 23 for each photodetector 21. In one embodiment, the back end circuitry 25 is configured and adapted to process the output signals of the front end circuitry 23 for each photodetector 21 in sequence. Moreover, the output of the back end circuitry 25 may combine the outputs of the front end circuitry 23 for each photodetector 21 into a single channel such that the detector module 20 can provide a single output requiring a single interconnection to other devices external to the module 20 as opposed to having a channel for each photodetector 21. While exemplary embodiments provide a multiplexing scheme that reduces the number of outputs to a single channel, those skilled in the art will recognize that other multiplexing schemes can be used. For example, in other exemplary embodiments outputs of the front end circuitry can be multiplexed into two or more channels. For the embodiments in which two channels are provided, for example, output signals from front end circuitry associated with each photodetector 21 in a first group can be multiplexed by back end circuitry common to the first group and output signals from front end circuitry associated with each photodetector 21 in a second group can be multiplexed by back end circuitry common to the second group.

Figure 7:
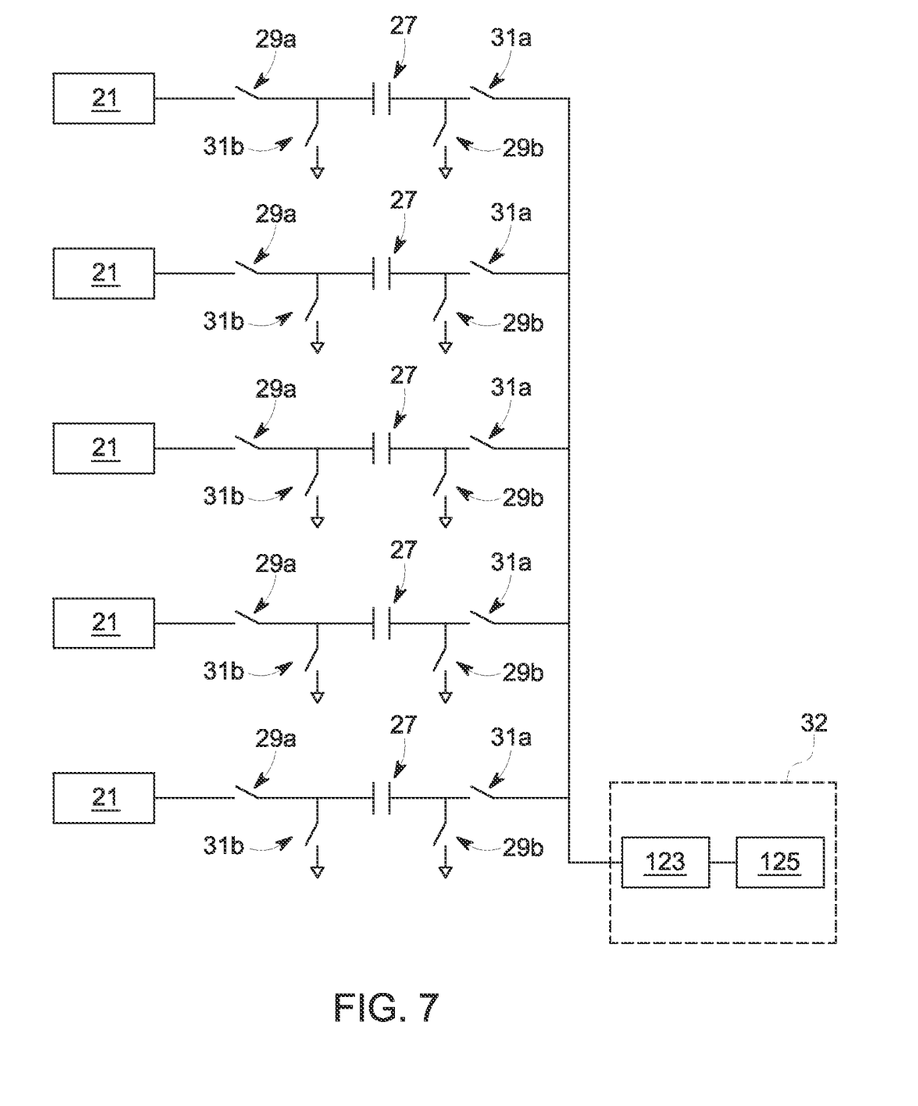
FIG. 7 is a partial block diagram of photodetectors and electronic components of an image sensor assembly/detector module in accordance with another exemplary embodiment of the present disclosure.

In another exemplary embodiment and as shown in FIG. 7, each photodetector may be in electrical communication with an energy storage device 27 (e.g., capacitor), with each energy storage device 27 in electrical communication with front end circuitry 123 that is common to each photodetector (i.e., the same front end circuitry is used to process signal from each photodetector). In certain embodiments, the front end circuitry 123 may process the charge from each energy storage device 27 in sequence. In general and as shown in FIG. 7, back end circuitry 125 is in electrical communication with the front end circuitry 123, each of which form the DAS and signal processing electronic components 32. The energy storage devices 27 (e.g., storage capacitors) associated with the electronic components 32 may help overcome the limitation of energy discrimination of systems 10 using kv switching or the like.

In an exemplary operation switches 29a and 29b can be closed to selectively place the photodetectors 21 in electrical communication with energy storage devices 27 and the switches 31a and 31b can be open so that the energy storage devices 27 are not in electrical communication with the front end circuitry 123. When one or more of the photodetectors 21 detect a light event, the photodetectors 21 that detected the light event can output a signal having an electrical charge to their corresponding energy storage devices 27, which can store the electrical charge. After the light event has been detected and the charge has been stored on the energy storage elements 27, the switches 29a and 29b can be open to electrically isolate the energy storage elements 27 from the photodetectors and each pair of switches 31a and 31b can be closed in sequence to sequentially place each of the energy storage elements 27 in electrical communication with the front end circuitry 123 to transfer the electrical charge from each of the energy storage devices 27 to the front end circuitry one at a time. For example, one of the pairs of the switches 31a and 31b can be closed to transfer the electrical charge from the corresponding energy storage device 27 to the front end circuitry while the other switches 31a and 31b remain open. After the charge has been transferred, the corresponding switches can be open again and the next pair of switches 31a and 31b can be closed to transfer the charge to the front end circuitry 123. This process can repeat until the charge from each energy storage device 27 is transferred to the front end circuitry 123. In exemplary embodiments, each pair of switches 29a and 29b can operate in unison and each pair of switches 31a and 31b can operate in unison.

As noted above, the present disclosure advantageously eliminates/reduces the interconnect by fabricating the electronics 32 and the photodetector 21 array on the same substrate 56 (e.g., the electronics 32 are fabricated in the gaps between photodiodes 21 of the substrate 56). Such an approach also reduces costs, since the photodetectors 21 and the electronics 32 are fabricated at substantially the same time. It also reduces interconnect capacitance between the photodetector 21 array and the electronics 32, thereby greatly improving performance in terms of noise, speed and power dissipation. Such an approach is also one of the keys in improving the problems associated with the trend of having an increasing number of pixels in a CT detector/system 10.

Moreover, the systems, assemblies and methods of the present disclosure substantially overcome the interconnect bottleneck between photodetectors 21 and their associated electronics 32. The systems, assemblies and methods of the present disclosure also reduce power dissipation, reduce noise and increase speed due to, inter alia, the reduced interconnect capacitance. The systems, assemblies and methods of the present disclosure also allow for the multiplexing of several pixels into a single channel of electronics to reduce power. The systems, assemblies and methods of the present disclosure also reduce costs by substantially eliminating the interconnect, and reduce/eliminate expensive thermal management. Moreover, the systems, assemblies and methods of the present disclosure enable an integrated digital sensor 20 which improves robustness to interference.

Although the systems, assemblies and methods of the present disclosure have been described with reference to exemplary embodiments thereof, the present disclosure is not limited to such exemplary embodiments and/or implementations. Rather, the systems, assemblies and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the claims be construed broadly and in a manner consistent with the scope of the disclosure.

What is claimed is:

1. An image sensor assembly comprising:
a semiconductor substrate comprising a top planar portion and a bottom planar portion;
a plurality of photodetectors comprising one or more contacts disposed on the top planar portion of the semiconductor substrate, the plurality of photodetectors in electrical communication with data acquisition and signal processing electronic components on the semiconductor substrate, wherein the contacts of the photodetectors, data acquisition and signal processing electronic components are co-located on the top planar portion of the semiconductor substrate;
a structured scintillator assembly disposed over the plurality of photodetectors; and
a collimator assembly positioned above the structured scintillator assembly with respect to the plurality of photodetectors and the data acquisition and signal processing electronic components, wherein the data acquisition and signal processing electronic components are disposed between the top planar surface of the semiconductor substrate and the collimator assembly, wherein an imaginary line, perpendicular to the top planar portion of the semiconductor substrate, intersects the collimator assembly, the structured scintillator and at least one of the data acquisition and signal processing electronic components;
wherein a layout of the photodetectors and the data acquisition and signal processing electronic components and a structural configuration of the collimator assembly are defined with respect to each other, and thereby eliminate an interconnect between the electronic components and the photodetector.

2. The assembly of claim 1, wherein at least a portion of the collimator assembly is positioned over at least a portion of the data acquisition and signal processing electronic components on the semiconductor substrate to shield at least a portion of the data acquisition and signal processing electronic components from radiation.

3. The assembly of claim 1, wherein the semiconductor substrate includes a plurality of dimpled areas, the scintillator conforming to the dimpled areas, the dimpled areas narrowing in area from a top side to a bottom side of the scintillator assembly.

4. The assembly of claim 1, further comprising:
a passivation layer deposited over the semiconductor substrate and comprising a second top planar portion and a second bottom planar portion where the second bottom planar portion of the passivation layer is affixed to the first top planar portion of the semiconductor substrate;
wherein the structured scintillator assembly is disposed over the plurality of the second top planar portion of the passivation layer.

5. The assembly of claim 1, wherein the data acquisition and signal processing electronic components further comprises:
front end circuitry for each photodetector; and
back end circuitry in electrical communication with the front end circuitry;
wherein the back end circuitry is configured to multiplex the output signals of the front end circuitry for each photodetector.

6. The assembly of claim 5, wherein the back end circuitry is configured to process the output signals in sequence.

7. The assembly of claim 5, wherein the output of the back end circuitry combines the outputs of the front end circuitry for each photodetector into a single channel.

8. The assembly of claim 1, wherein each photodetector is in electrical communication with an energy storage device, each energy storage device in electrical communication with front end circuitry; and wherein the front end circuitry processes the charge from each energy storage device in sequence.

9. The assembly of claim 1, wherein a quantity of the photodetectors are adapted to be selectively combined to form one or more pixels.

10. A method of fabricating an image sensor assembly comprising:
providing a semiconductor substrate comprising a top planar portion and a bottom planar portion;
disposing a plurality of photodetectors comprising one or more contacts on the top planar portion of the semiconductor substrate;
integrating data acquisition and signal processing electronic components on the semiconductor substrate, the data acquisition and signal processing electronic components in electrical communication with the plurality of photodetectors, wherein the contacts of the photodetectors, data acquisition and signal processing electronic components are co-located on the top planar portion of the semiconductor substrate;
positioning a structured scintillator assembly over the plurality of photodetectors; and
positioning a collimator assembly above the structured scintillator with respect to the plurality of photodetectors and the data acquisition and signal processing electronic components, wherein the data acquisition and signal processing electronic components are disposed between the top planar surface of the semiconductor substrate and the collimator assembly, wherein an imaginary line, perpendicular to the top planar portion of the semiconductor substrate, intersects the collimator assembly, the structured scintillator and at least one of the data acquisition and signal processing electronic components;
wherein a layout of the photodetectors and the data acquisition and signal processing electronic components and a structural configuration of the collimator assembly are defined with respect to each other, and thereby eliminate an interconnect between the electronic components and the photodetector.

11. The method of claim 10, wherein at least a portion of the collimator assembly is positioned over at least a portion of the data acquisition and signal processing electronic components on the semiconductor substrate to shield at least a portion of the data acquisition and signal processing electronic components from radiation.

12. The method of claim 10, wherein the semiconductor substrate includes a plurality of dimpled areas, the scintillator conforming to the dimpled areas, the dimpled areas narrowing in area from the top side to the bottom side of the scintillator assembly.

13. The method of claim 10, further comprising the step of incorporating the fabricated image sensor assembly into a detector assembly of an imaging system.

14. The method of claim 10, wherein the data acquisition and signal processing electronic components include front end circuitry for each photodetector and back end circuitry in electrical communication with the front end circuitry, and the method further comprises configuring the back end circuitry to multiplex the output signals of the front end circuitry for each photodetector.

15. The method of claim 10, further comprising:
disposing a plurality of energy storage devices on the semiconductor substrate, each photodetector being in electrical communication with one of the energy storage devices, each energy storage device in electrical communication with front end circuitry; and
configuring the front end circuitry to process the charge from each energy storage device in sequence.

16. The method of claim 10, further comprising selectively combining a quantity of the photodetectors to form one or more pixels.

17. An imaging system comprising:
an x-ray source; and
an image sensor assembly including:
(a) a semiconductor substrate comprising a top planar portion and a bottom planar portion;
(b) a plurality of photodetectors comprising one or more contacts on the top planar portion of the semiconductor substrate, the plurality of photodetectors in electrical communication with data acquisition and signal processing electronic components on the semiconductor substrate, wherein the contacts of the photodetectors, data acquisition and signal processing electronic components are co-located on the top planar portion of the semiconductor substrate;
(c) a structured scintillator assembly disposed over the plurality of photodetectors; and
(d) a collimator assembly positioned above the structured scintillator assembly with respect to the plurality of photodetectors and the data acquisition and signal processing electronic components, wherein the data acquisition and signal processing electronic components are disposed between the top planar surface of the semiconductor substrate and the collimator assembly, wherein an imaginary line, perpendicular to the top planar portion of the semiconductor substrate, intersects the collimator assembly, the structured scintillator and at least one of the data acquisition and signal processing electronic components;
wherein the scintillator assembly is configured to: (i) receive x-rays that pass through an object, the x-rays emitted from the x-ray source, and (ii) release light at an intensity in response to reception of x-rays;
wherein each photodetector of the plurality of photodetectors is configured to provide an electrical signal indicative of the intensity of the light released by the scintillator assembly and received by each photodetector; and
wherein a layout of the photodetectors and the data acquisition and signal processing electronic components and a structural configuration of the collimator assembly are defined with respect to each other, and thereby eliminate an interconnect between the electronic components and the photodetector.

18. The system of claim 17, wherein at least a portion of the collimator assembly is positioned over at least a portion of the data acquisition and signal processing electronic components on the semiconductor substrate to shield at least a portion of the data acquisition and signal processing electronic components from radiation.

19. The system of claim 17, wherein the semiconductor substrate includes a plurality of dimpled areas, the scintillator assembly conforms to the dimpled areas, the dimpled areas narrowing in area from a top side to a bottom side of the scintillator assembly.

20. The system of claim 17, wherein the data acquisition and signal processing electronic components further comprise:
front end circuitry for each photodetector; and
back end circuitry in electrical communication with the front end circuitry;

wherein the back end circuitry is configured to multiplex the output signals of the front end circuitry for each photodetector, process the output signals in sequence, and combine the outputs of the front end circuitry for each photodetector into a single channel.

* * * * *